(12) United States Patent
Sumida et al.

(10) Patent No.: US 6,504,054 B1
(45) Date of Patent: Jan. 7, 2003

(54) AMINO ACID DERIVATIVE AND PRODUCING METHOD THEREOF

(75) Inventors: Yasutaka Sumida, Neyagawa (JP); Mitsuhiro Kitajima, Suita (JP); Tomomi Ina, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/655,043

(22) Filed: Sep. 5, 2000

(30) Foreign Application Priority Data

Sep. 3, 1999 (JP) .......................................... 11-249888
Nov. 2, 1999 (JP) .......................................... 11-312239

(51) Int. Cl.[7] .......................................... C07C 229/00
(52) U.S. Cl. ...................................... 562/568; 562/571
(58) Field of Search ........................... 562/507, 508, 562/509, 553, 568, 571

(56) References Cited

FOREIGN PATENT DOCUMENTS

| EP | 591934 A1 * | 4/1994 | ............ G03C/5/305 |
| EP | 0 984 101 A1 | 3/2000 | |
| JP | 06059422 | 3/1994 | |
| JP | 08-208569 A2 * | 8/1996 | ......... C07C/217/08 |
| WO | WO 97/45396 | 12/1997 | |
| WO | WO 99/25919 | 5/1999 | |
| WO | WO 00/26398 | 5/2000 | |

OTHER PUBLICATIONS

N.N. Abramovskaya, "Synthesis and Study of Hydroxyethyl Derivatives of Momoamine–Type Complexing Agents", Probl. Khim. Kompleksonov, I.P. Gorelov (editor), Kalinin. Gos. Univ. (pub), 1985, pp 108–115.*

Krzysztof Jankowski et al, "Preparation of N–(2–Hydroxyalkyl)–2–Morpholones and N,N–bis(2–Hydroxyalkyl)amino Acids", Bull. Acad. Pol. Sci., Ser. Sci. Chim. 1970, pp 183–192.*

Synthèse de morpholones–2, des hydroxyaminoacides correspondants et de leurs chélates cuivriques, à partir de époxydes–1,2 et des sels de sodium d'α–aminoacides; Maurice L. Pascal, pp. 435–442 (1959).

Chemical Abstracts 108: 37203t *Synthesis and study of hydroxyethyl derivatives of monamine–type complexing agents*; vol. 108 (1988).

* cited by examiner

Primary Examiner—Paul J. Killos
(74) Attorney, Agent, or Firm—Connolly Bove Lodge & Hutz LLP (57) ABSTRACT

An amino acid derivative composition which comprises two or more kinds of amino acid derivatives represented by the general formula (1):

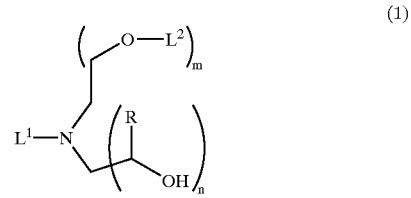

(1)

wherein R's are the same or different and each represents a hydrogen atom or an alkyl group containing 1 to 18 carbon atoms; $L^1$ represents —$M^1$—X or —CHX—$M^2$—X; $L^2$ represents —$CH_2$—$M^3$—X or —CHX—$M^4$—X; $M^1$, $M^2$, $M^3$ and $M^4$ are the same or different and each represents a straight or branched alkylene group containing 1 to 6 carbon atoms; X represents COOM; M's are the same or different and each represents a hydrogen atom, an alkali metal atom, an alkaline earth metal atom or an ammonium group; m represents an integer of 1 or 2 and n represents an integer of 0 or 1 on the condition that m+n is equal to 2 is provided.

5 Claims, 1 Drawing Sheet

Fig. 1

AMINO ACID DERIVATIVE AND PRODUCING METHOD THEREOF

CROSS-REFERENCE TO RELATED APPLICATIONS

This application claims foreign priority under 35 USC 119 from Japanese Applications 11-249888 filed Sep. 3, 1999 and 11-312239 filed Nov. 2, 1999.

FIELD OF THE INVENTION

The present invention relates to a composition or compound each having a tertiary amine structure and having chelate effects and biodegradability, to a process for producing said composition or compound, and to a chelating agent comprising said composition or compound. More particularly, the invention relates to an amino acid derivative composition and a process for producing an amino acid derivative. The present invention also relates to an L-aspartic acid derivative, a process for producing an L-aspartic acid derivative, an L-aspartic acid derivative composition, a process for producing an L-aspartic acid derivative composition, and a chelating agent. The invention further relates to a process for producing N-bishydroxyalkyl-amino acids and a process for producing N-bishydroxyethylaspartic acids.

PRIOR ART

Chelating agents can sequester metal ions by forming 2 or more coordinate bonds and therefore are used for eliminating harmful influences exerted by the presence of metal ions in various fields, such as in the fields of detergents, textiles, paper and pulp, metal surface treatment and photography, among others, and they are now indispensable to chemical industries and daily life.

In the field of detergents, for instance, chelating agents are used to remove metal ions, such as calcium and magnesium ions, in hard water for rendering the water usable for the intended purpose and, in the field of textiles, paper and pulp, for instance, they are used to prevent hydrogen peroxide and like bleaching agents from being decomposed in the presence of metal ions. As typical chelating agents, there may be mentioned, among others, ethylenediaminetetraacetic acid (EDTA) and the like, which are inexpensive and are high in chelating power.

These chelating agents are disposed of in a state contained in household waste water and industrial waste. Therefore, if they are hardly biodegradable, they may have unfavorable influences on the environment and ecological system. Generally, the term "biodegradability" means that a substance can be decomposed spontaneously by microorganisms or products thereof in nature and the decomposition products do not have harmful influences on the environment and ecosystem any longer.

In recent years, the regulations against environmental pollution by chemical substances have become more and more strict. The current situation is such that the use of those chelating agents which are lacking in biodegradability is hesitated. Therefore, various investigations are in progress in search of chelating agents having improved biodegradability.

Japanese Kokai Publication Hei-08-208569 discloses the technology of using a diethanolamine derivative as a chelating agent. This diethanolamine derivative is produced by reacting diethanolamine with maleic acid and/or a salt thereof in the presence of an alkaline earth metal. Its carboxyl groups occurring around the nitrogen atom and the ether group-derived oxygen atom, which serve as central atoms, effectively produce its chelating activity. Furthermore, the derivative has such a high level of biodegradability that none of the conventional chelating agents can be equal to it in that respect. However, there is still room for improvement in chelating effect and biodegradability.

Japanese Kohyo Publication Hei-10-502632 discloses a process for producing salts of [S,S]-ethylenediamine-N,N'-disuccinic acid (ss-EDDS) which comprises the step of reacting L-aspartic acid with a 1,2-dihaloethane in a basic aqueous solution in which the amount of 1,2-dihaloethane is stoichiometrically insufficient throughout the reaction period so that less than 60 mole percent of the initial charge of L-aspartic acid can react. It has been found that the sodium salt of the above ss-EDDS is useful as a biodegradable chelating agent. However, in view of the chemical structure of ss-EDDS, there is still room for technical improvement for producing the chelating activity more efficiently or increasing the biodegradability.

Laid-open International Patent Specification WO 97/45396 discloses an N-bis- or N-tris[(1,2-dicarboxyethoxy)-ethyl]-amine derivative as a biodegradable chelating agent. This amine derivative can be produced by reacting di- or triethanolamine with maleic acid in the presence of an alkali metal or alkaline earth metal salt, using a lanthanide compound, a lanthanide compound mixture or an alkaline earth metal compound as a catalyst. However, such compounds have two or more asymmetric carbon atoms but their configurations have not been specified as yet. It is thus difficult to expect that they are surely biodegradable.

Japanese Kokai Publication Hei-06-59422 discloses a treatment composition for silver halide-containing photosensitive materials which contains an N-bishydroxyethylaspartic acid salt or the like as a chelating agent. Since the N-bishydroxyethylaspartic acid salt or the like has a chelating activity, this treatment composition is suited for rapid treatment with efficient desilverization. Since said salt or the like has biodegradability, the possibility of environmental pollution by the composition is much less. Thus, N-bishydroxyethylaspartic acids are themselves useful as chelating compounds. In recent years, they have been regarded as promising also as intermediates for the production of compounds having the basic skeleton of aspartic acid within the molecule.

A process for producing these N-bishydroxyethylaspartic acids is disclosed in Problemy Khimii Kompleksonov (1985) (in Russian), pp. 108–115. This process comprises the step of esterifying aspartic acid in a methanol/hydrochloric acid solution to give dimethyl aspartate, the step of causing ethylene oxide to add to dimethyl aspartate and the subsequent step of hydrolyzing the addition product with sodium hydroxide or the like. This process, however, involves a number of steps, hence byproduct formation is highly possible. Further, the production cost is high and it is difficult to expect improvements in yield.

SUMMARY OF THE INVENTION

It is an object of the present invention, which has been made in view of the above-mentioned state of the art, to provide a composition or compound having sufficient chelating activity and remarkably high biodegradability, a process for producing said composition or compound, and a chelating agent comprising said composition or compound. Another object of the present invention is to provide a simplified process for producing N-bishydroxyalkyl-amino acids having chelating activity and biodegradability in improved yields while reducing the possibility of byproduct formation.

The present invention provides an amino acid derivative composition which comprises two or more kinds of amino acid derivatives represented by the general formula (1):

(1)

wherein R's are the same or different and each represents a hydrogen atom or an alkyl group containing 1 to 18 carbon atoms; $L^1$ represents $-M^1-X$ or $-CHX-M^2-X$; $L^2$ represents $-CH_2-M^3-X$ or $-CHX-M^4-X$; $M^1$, $M^2$, $M^3$ and $M^4$ are the same or different and each represents a straight or branched alkylene group containing 1 to 6 carbon atoms; X represents COOM; M's are the same or different and each represents a hydrogen atom, an alkali metal atom, an alkaline earth metal atom or an ammonium group; m represents an integer of 1 or 2 and n represents an integer of 0 or 1 on the condition that m+n is equal to 2.

The present invention also provides a process for producing the amino acid derivative represented by the above general formula (1) (wherein R represents a hydrogen atom or an alkyl group containing 1 to 18 carbon atoms; $L^1$, $L^2$, $M^1$, $M^2$, $M^3$, $M^4$, X, m and n are defined as above) which comprises the steps of:

causing an alkylene oxide to add to an amino acid and reacting the amino acid-alkylene oxide adduct with an unsaturated carboxylic acid in the presence of a rare earth-based catalyst.

The present invention further provides a chelating agent which comprises the amino acid derivative composition.

The invention also provides an L-aspartic acid derivative represented by the general formula (2):

(2)

wherein X, m and are as defined above and * indicates that the asymmetric carbon atom carrying this symbol is in S configuration.

The invention further provides a process for producing the above L-aspartic acid derivative
which comprises the steps of:

causing ethylene oxide to add to L-aspartic acid and reacting the resulting L-aspartic acid-ethylene oxide adduct with maleic acid in the presence of a rare earth-based catalyst.

The invention still further provides a chelating agent which comprises the above L-aspartic acid derivative.

The invention also provides an L-aspartic acid derivative composition which comprises an L-aspartic acid derivative (A) and an L-aspartic acid derivative (B),
said derivative (A) being represented by the general formula (3):

(3)

wherein X is as defined above and * indicates that the asymmetric carbon atom carrying this symbol is in S configuration,
and said derivative (B) being represented by the general formula (4):

(4)

wherein X is as defined above and indicates that the asymmetric carbon atom carrying this symbol is in S configuration, wherein, in said L-aspartic acid derivative composition, the occurrence ratio (mole ratio) between said derivative (A) and said derivative (B) is in the range of 1:99 to 99:1.

The present invention further provides a process for producing the above L-aspartic acid derivative composition which comprises the steps of:

causing ethylene oxide to add to L-aspartic acid and reacting the resulting L-aspartic acid-ethylene oxide adduct with maleic acid in the presence of a rare earth-based catalyst.

The invention still further provides a chelating agent which comprises the above L-aspartic acid derivative composition.

The invention further provides a process for producing N-bishydroxyalkyl-amino acids represented by the general formula (5):

(5)

wherein R represents a hydrogen atom or an alkyl group containing 1 to 18 carbon atoms; $L^1$, $M^1$, $M^2$ and X are as defined above, which comprises the step of causing an alkylene oxide to add to an amino acid salt in an aqueous solution.

Finally, the invention provides a process for producing N-bishydroxyethylaspartic acids represented by the general formula (6):

wherein X is as defined above,
which comprises the step of causing ethylene oxide to add to an aspartic acid salt in an aqueous solution.

DETAILED DESCRIPTION OF THE INVENTION

In the following, the present invention is described in detail.

The amino acid derivative composition according to the present invention comprises two or more amino acid derivatives represented by the above general formula (1).

In the above amino acid derivative composition, the total content of the amino acid derivatives represented by the general formula (1) is not particularly restricted so long as the effects of the invention can be produced. They are contained in the composition preferably as main components. Another or other components may or may not be additionally contained therein. For example, the total content of the amino acid derivatives of general formula (1) is preferably 50 to 100% by weight, more preferably 70 to 100% by weight, still more preferably 90 to 100% by weight.

In the above general formula (1), R's are the same or different and each represents a hydrogen atom or an alkyl group containing 1 to 18 carbon atoms. When the number of carbon atoms is greater than 18, it may possibly become difficult to produce the intended amino acid derivatives and the derivatives may possibly fail to show sufficient chelating activity. $L^1$ represents —$M^1$—X or —CHX—$M^2$—X. $L^2$ represents —$CH_2$—$M^3$—X or —CHX—$M^4$—X. $M^1$, $M^2$, $M^3$ and $M^4$ are the same or different and each represents a straight or branched alkylene group containing 1 to 6 carbon atoms. When the number of carbon atoms exceeds 6, the resulting amino acid derivatives will have insufficient chelating activity. X is a carboxyl group or a substituted carboxyl group. M's are the same or different and each represents a hydrogen atom, an alkali metal atom, an alkaline earth metal atom or an ammonium group. The symbol m represents an integer of 1 or 2. The symbol n represents an integer of 0 or 1. The sum m+n is equal to 2, however. Therefore, it is one of the features of the amino acid derivatives according to the invention from the chemical structure viewpoint that two or more carboxyl or substituted carboxyl groups and the nitrogen atom and ether group-derived oxygen atom occur within one and the same molecule.

The alkyl group represented by R is not particularly restricted but includes, among others, methyl, ethyl, propyl, n-butyl, pentyl, hexyl, heptyl, octyl, nonyl, decyl, undecyl, dodecyl, tridecyl, tetradecyl, pentadecyl, hexadecyl, heptadecyl, octadecyl, etc. Among them, alkyl groups containing 1 to 12 carbon atoms are preferred. More preferred are alkyl groups containing 1 to 6 carbon atoms and still more preferred are alkyl groups containing 1 to 3 carbon atoms. $M^1$, $M^2$, $M^3$ and $M^4$ are not particularly restricted, either. Preferred are, however, straight or branched alkylene, groups containing 1 to 4 carbon atoms, for example methylene, ethylene, propylene and butylene.

The alkali metal atom mentioned above is not particularly restricted but includes lithium, sodium, potassium, rubidium, cesium and francium. Among them, sodium and potassium are preferred, however, because of their ready availability and inexpensiveness. The above alkaline earth metal atom is not particularly restricted but includes beryllium, magnesium, calcium, strontium, barium and radium. Magnesium and calcium are preferred, however, because of their ready availability and inexpensiveness.

Based on their characteristic chemical structure, the above amino acid derivatives can serve as at least tetraentate ligands to metal ions and, therefore, the amino acid derivative composition of the present invention show good chelating activity. When it contains a compound in which n is 0 and m is 2, the amino acid derivative composition of the invention expresses still better chelating activity since the coordination number to metal ions can be further increased.

The chelating activity of the amino acid derivative composition of the invention can be measured by various methods. For example, it can be measured in the following manner.
(1) Evaluation of Chelating Performance Against $Ca^{2+}$ The chelating performance against $Ca^{2+}$ can be evaluated in terms of $Ca^{2+}$ trapping ability by the calcium ion-selective electrode method mentioned below.
[1] 2 ml of 4 M KCl is added to 100 ml of $10^{-3}$ M $CaCl_2$ solution.
[2] 10 mg of the sample is added to the above solution, and the solution is adjusted to pH 10 with 0.1 M KOH (or 0.1 M HCl) and maintained at 25° C.
[3] The $Ca^{2+}$ concentration is measured using a calcium ion-selective electrode.
[4] The $Ca^{2+}$ trapping ability is calculated in terms of the amount of $Ca^{2+}$ trapped based on the result of $Ca^{2+}$ concentration measurement.
(2) $H_2O_2$ Stabilization Test Measurements can be made as follows. Measurement method: The stability of $H_2O_2$ in the alkaline region in the presence of $Fe^{3+}$ is measured by following the course of change with time of the residual $H_2O_2$ in percentage. Measurement conditions: pH 10, 50° C., $Fe^{3+}$ concentration 2 ppm, initial quantity of $H_2O_2$ 3 g/l, sample concentration 200 ppm.

By evaluating the $Ca^{2+}$ chelating capacity in the above manner, it is possible to estimate the chelating performance (chelating activity) in terms of calcium ion ($Ca^{2+}$) trapping ability. The chelating performance (chelating activity) can be evaluated by the above $H_2O_2$ stabilization test with the heavy metal ion sequestering ability as a measure.

The biodegradability of the amino acid derivative composition of the invention can be measured by various methods. For example, it can be measured by any of the following test methods prescribed in the OECD Guideline 301 (ready degradability):
Test method 301A: DOC Die-Away test
Test method 301B: $CO_2$ emission test (modified Sturm test)

Test method 301C: Modified MITI test (I)
Test method 301D: Closed bottle test
Test method 301E: Modified OECD screening test
Test method 301F: Manometric respirometry test

Among these, the test method 301C: Modified MITI test (I) is preferred.

According to these test methods, biodegradability evaluation can be made by measuring such parameters as Dt (decomposition degree), BOD (biochemical oxygen demand) and $CO_2$ emission generally for consecutive 28 days.

The amino acid derivative composition according to the present invention has marked chelating activity as well as high biodegradability.

Why such excellent chelating activity is exhibited is no doubt associated with the positions of the carboxyl groups or substituted carboxyl groups and the number of such groups in the molecules contained in the amino acid derivative composition.

For the amino acid derivatives according to the invention to have improved chelating activity, it is preferred, for instance, that they have the group:

wherein X is as defined above, and it is more preferred that they have this group in large numbers within the molecule.

For attaining increased chelating activity with the amino acid derivatives to be used in accordance with the present invention, it is preferred, for example, that there are a plurality of groups of the formula:

wherein X is as defined above, within the molecule and it is more preferred that the groups occur in positions closer with each other.

For the amino acid derivatives according to the invention to have an elevated level of biodegradability, it is preferred, for example, that the group represented by $L^1$ be —CHX—$M^2$—X and the asymmetric carbon atom in this group be in S configuration.

The reasons why the amino acid derivative composition according to the invention shows biodegradability are not fully clear. However, the following reasons, for instance, are plausible:
(1) That compounds having a tertiary amine structure, when an atom or group of atoms readily undergoing biodegradation is bonded to the tertiary amine-constituting nitrogen atom, are presumably susceptible to biodegradation; (2) that the occurrence of a hydroxy group leads to ready biodegradability; (3) that when the group $L^1$ is —CHX—$M^2$—X and the asymmetric carbon atom in this group is in S configuration, the possibility of the asymmetric carbon atom in S configuration undergoing biodegradation is essentially higher as compared with the asymmetric carbon atom in R configuration since the asymmetric carbon atoms in naturally occurring compounds have in principle the S configuration; and (4) that since biodegradation of a compound seemingly proceeds in the manner of chain reaction once one atom or atomic group forming the compound has undergone biodegradation, compounds having at least one readily biodegradable atom or atomic group are considered to be readily biodegradable.

In other words, it is presumable that the above amino acid derivatives acquire an elevated level of biodegradability owing to its tertiary amine structure itself and, in addition, that since when, for example, m in general formula (1) is 1 and n is 1, they have a hydroxy group and, when the group represented by $L^1$ is —CHX—$M^2$—X and the asymmetric carbon atom in this group is in S configuration, they have an asymmetric carbon atom in S configuration with the asymmetric carbon atom in S configuration being bonded to the nitrogen atom in their tertiary amine structure, they, which have such a hydroxy group and such an asymmetric carbon atom that are readily biodegradable, may effectively be biodegraded. It is further considered that when such hydroxyl group and asymmetric carbon atom are biodegraded, the derivatives are biodegraded in a chain reaction manner, manifesting a high level of biodegradability.

The amino acid derivatives according to the present invention which are represented by the general formula (1) are amino acid derivatives (A) resulting from addition of one molecule of an unsaturated carboxylic acid when, for example, m is 1 and n is 1 and, when m is 2 and n is 0, they are amino acid derivatives (B) resulting from addition of two molecules of an unsaturated carboxylic acid. Therefore, according to the values of m and n, the above two classes are possible as the amino acid derivatives in the amino acid derivative composition of the present invention. These two classes each further 1includes various subclasses of amino acid derivatives according to the species of R, $L^1$, $L^2$, $M^1$, $M^2$, $M^3$, $M^4$ and M. The amino acid derivative composition of the invention comprises two or more of those amino acid derivatives.

Among the amino acid derivatives in the amino acid derivative composition of the present invention, that compound of general formula (1) in which n is 1, m is 1, R is a hydrogen atom, $L^1$ is —CHX—$M^2$—X, $L^2$ is —CHX—$M^4$—X, $M^2$ and $M^4$ each is methylene, X is COOM and M is a hydrogen atom and in which the asymmetric carbon atom has an unspecified configuration is the compound designated as BCEEAA in the above-cited laid-open International Patent Specification WO 97/45395. However, the amino acid derivative composition of the present invention comprises at least two of the above-mentioned amino acid derivatives and has excellent chelating activity as a result of the synergy between them and, in addition, shows high biodegradability, hence differs from said BCEEAA in composition as well as in effect or efficacy.

The process for producing the amino acid derivative composition of the invention is not particularly restricted but the composition can be produced, for example, by a process comprising the step of causing an alkylene oxide to add to an amino acid and the step of reacting the resulting amino acid-alkylene oxide adduct with an unsaturated carboxylic acid in the presence of a rare earth-based catalyst.

According to the above production process, it is possible to produce one amino acid derivative represented by the general formula (1) by one operation procedure and thus produce two or more amino acid derivatives by two or more operational procedures and then produce the amino acid derivative composition according to the invention by blending the two or more amino acid derivatives. It is also possible to produce the amino acid derivative composition comprising two more amino acid derivatives of general formula (1) by one operational procedure. In the practice of the present invention, it is preferred that the above composition be produced by one procedure. Thereby the amino acid derivative composition comprising two or more amino acid derivatives represented by the general formula (1) can be produced in a simple and easy manner.

The process for producing amino acid derivatives represented by the general formula (1) which comprises the step of causing an alkylene oxide to add to an amino acid and the step of reacting the resulting amino acid-alkylene oxide adduct with an unsaturated carboxylic acid in the presence of a rare earth-based catalyst can give the desired amino acid derivatives in high yields while simplifying the production steps and reducing the possibility of byproduct formation.

Typical examples of the above steps are as follows.

In the present specification, the step of causing an alkylene oxide to add to an amino acid is referred to also as "alkylene oxide addition step", and the step of reacting the amino acid-alkylene oxide adduct with an unsaturated carboxylic acid in the presence of a rare earth-based catalyst is referred to also as "unsaturated carboxylic acid addition step".

In the above reaction formula, R; $L^1$, $L^2$, $M^1$, $M^2$, $M^3$, $M^4$, X, m and n are as defined above.

In the alkylene oxide addition step, an alkylene oxide adduct (general formula (7) given above) is generally formed as a result of substitution of both the two hydrogen atoms of the amino group of the starting material amino acid by the alkylene oxide. The thus-formed alkylene oxide adduct of general formula (7) can be reacted with an unsaturated carboxylic acid in the manner of addition reaction to give the desired carboxylic acid adduct. The carboxylic acid adduct obtainable by such a reaction includes two classes, namely the carboxylic acid adduct 1 (general formula (8) given above) resulting from addition of one molecule of the unsaturated carboxylic acid, and the carboxylic acid adduct 2 (general formula (9) given above) resulting from addition of two molecules of the unsaturated carboxylic acid.

The above-mentioned amino acid derivative production process also constitutes an aspect of the present invention.

According to the amino acid derivative production process according to the present invention, there is no possibility at all of the formation of compounds represented by the general formula (10):

(10)

wherein X is as defined above.

In this respect, the amino acid derivative production process according to the present invention is quite different from the production process disclosed in Laid-open International Patent Specification WO 97/45396. Further, the compounds represented by the above general formula (10) are poor in chelating activity and in biodegradability, hence are compounds entirely different from the amino acid derivatives in the amino acid derivative composition according to the present invention.

The amino acid to be used in the above alkylene oxide addition step is not particularly restricted but includes, among others, aspartic acid, glutamic acid, glycine, methylglycine and β-alanine. These may be used singly or two or more of them may be used in combination. Among these, aspartic acid and glutamic acid are preferred since the product amino acid derivatives have high chelating activity. Aspartic acid is more preferred. The above amino acid may be in L form or in D form or in the form of a mixture, for example a racemic mixture. The L form is preferred, however, since it is less expensive than the racemic form or D form. When the amino acid is used in L form, the L form configuration is retained, namely the L-form-derived configuration is retained as it is in the product as the S configuration on the asymmetric carbon atom in the structural formula, and the resulting amino acid derivative composition becomes excellent in biodegradability. Hence, the L form is preferred. Therefore, in the practice of the present invention, the use of L-aspartic acid as the amino acid is most preferred.

The above alkylene oxide is not particularly restricted but includes, among others, ethylene oxide and propylene oxide. These may be used singly or two or more of them may be used combinedly. Among them, ethylene oxide is preferred since it is superior in reactivity.

The unsaturated carboxylic acid to be used in the above unsaturated carboxylic acid addition step includes, but is not particularly limited to, (meth)acrylic acid, maleic acid, maleic anhydride, fumaric acid, crotonic acid, itaconic acid and citraconic acid, among others. These may be used singly or two or more of them may be used combinedly. Among the unsaturated carboxylic acids, unsaturated dicarboxylic acids are preferred since the use thereof gives the product amino acid derivative an increased coordination number against metals. Among the unsaturated dicarboxylic acids, maleic acid, maleic anhydride and the like are preferred. For carrying out the reaction efficiently, the use of maleic anhydride as the raw material is preferred.

The rare earth-based catalyst to be used in the above unsaturated carboxylic acid addition reaction is not particularly restricted but generally has the form of oxide, hydroxide, chloride, nitrate, sulfate, oxalate or the like. As the rare earth element, there may be mentioned lanthanoid elements such as lanthanum, cerium, praseodymium and neodymium; scandium; yttrium and so forth. Among them, lanthanum is relatively inexpensive and readily available. Lanthanum oxide is thus preferred.

The mole ratio between the amino acid and alkylene oxide, which is to be employed in the above alkylene oxide addition step, is not particularly restricted but, for both hydrogen atoms of the amino group in the amino acid to be completely substituted by the alkylene oxide, it is preferred that the ratio (number of moles of alkylene oxide)/(number of moles of amino acid) amount to 2 to 10, more preferably 2.5 to 8, still more preferably 3 to 6.

In the above alkylene oxide addition step, the hydroxide or carbonate of an alkali metal, the hydroxide or carbonate of an alkaline earth metal, an ammonium group-containing compound or the like is preferably used for substituting the carboxyl hydrogen atom or atoms of the amino acid.

The amount of the compound to be used for substituting the carboxyl hydrogen atom or atoms of the amino acid is not particularly restricted but, for complete substitution of the carboxyl hydrogen atom or atoms of the amino acid, for instance, the above compound is used preferably in an amount not less than one equivalent per equivalent of the amino acid. For example, the above compound is used preferably in an amount of 1 to 3 equivalents, more preferably 1 to 2 equivalents, per equivalent of the amino acid.

In the above alkylene oxide addition step, the method of carrying out the reaction is not particularly restricted. Preferably, however, the reaction system is purged with an inert gas such as nitrogen gas and the reaction is carried out using a reaction medium. For controlling the reaction of the alkylene oxide, it is preferred that the alkylene oxide be added (dropwise) over a prolonged period of time.

The above reaction medium is not particularly restricted but is preferably an aqueous medium, for instance, more preferably water.

The amount of the above reaction medium is not particularly restricted but, generally, the reaction is carried out preferably in such a state that the amino acid salt is dissolved in the medium to give a homogeneous solution, for example at an amino acid salt concentration of about 40% by weight.

The period over which the above alkylene oxide is to be added (dropwise) is not particularly restricted. However, when ethylene oxide is used, for instance, a period of 0.5 to 6 hours is preferred and 1 to 5 hours is more preferred.

The reaction temperature and reaction time in the above alkylene oxide addition step are not particularly restricted. When ethylene oxide is used, for instance, the reaction temperature is preferably 15 to 80° C. and the reaction time after completion of the addition (dropping) of ethylene oxide is preferably 0.5 to 5 hours. More preferably, the reaction temperature is 20 to 60° C. and the reaction time after completion of the addition (dropping) of ethylene oxide is 1 to 4 hours.

The percent conversion of-the amino acid in the above alkylene oxide addition step is not particularly restricted but preferably amounts to not less than 60%, for instance, more preferably not less than 80%, still more preferably not less than 90%, most preferably not less than 95%.

In the above unsaturated carboxylic acid addition step, the mole ratio between the unsaturated carboxylic acid and amino acid-alkylene oxide adduct is not particularly restricted but preferably the ratio (unsaturated carboxylic acid)/(amino acid-alkylene oxide adduct) amounts to 0.5 to 4, more preferably 1 to 3.

In the above unsaturated carboxylic acid addition step, it is possible to adjust the mole ratio between the carboxylic acid adduct 1 and carboxylic acid adduct 2 in the amino acid derivative product by adjusting the mole ratio between the unsaturated carboxylic acid and amino acid-alkylene oxide adduct.

In the above unsaturated carboxylic acid addition step, the hydroxide or carbonate of an alkali metal, the hydroxide or carbonate of an alkaline earth metal, an ammonium group-containing compound or the like is preferably used for substitution of the carboxyl hydrogen atom or atoms of the unsaturated carboxylic acid. The amount of the compound to be used for substituting the carboxyl hydrogen atom or atoms of the unsaturated carboxylic acid is not restricted. For complete substitution of the carboxyl hydrogen atom or atoms of the unsaturated carboxylic acid, for instance, the above compound is preferably used in an amount of not less than one equivalent per equivalent of the unsaturated carboxylic acid. For example, the above compound is used preferably in an amount of 1 to 3 equivalents, more preferably 1 to 2 equivalents, per equivalent of the unsaturated carboxylic acid.

The method of carrying out the reaction in the above unsaturated carboxylic acid addition step is not particularly restricted. Preferably, however, the reaction is carried out while adjusting the pH of the reaction system.

The pH of the reaction system in the above unsaturated carboxylic acid addition step is not particularly restricted but is preferably not lower than 8, more preferably not lower than 9, still more preferably not lower than 9.5.

When it is intended that the carboxylic acid adduct 1 represented by the above general formula (8) and the carboxylic acid adduct 2 represented by the above general formula (9) be obtained in the form of an alkali metal salt, salt exchange is effected by adding the carbonate and/or bicarbonate of the corresponding alkali metal, for instance, to thereby cause precipitation of the carbonate of the rare earth contained in the system, followed by removing the precipitate by filtration, for instance, whereby the alkali metal salt of the above carboxylic acid adduct 1 and the alkali metal salt of the above carboxylic acid adduct 2 are obtained in the form of an aqueous solution.

The composition obtained in the above unsaturated carboxylic acid addition step can further be separated into the respective components, and each amino acid derivative can be isolated.

The method of the above isolation is not particularly restricted. For example, after conversion of all carboxyl groups to the acid form by acid treatment, the carboxylic acid adduct 1 and the carboxylic acid adduct 2 can be recovered each in the acid form by carrying out a chromatographic procedure using a column packed with a basic anion exchange resin and using an aqueous solution of formic acid, for instance, as the eluent.

The amino acid derivative composition comprising the carboxylic acid adduct 1 and the carboxylic acid adduct 2, when the occurrence ratio between the adducts 1 and 2 is within a predetermined specific range is a very useful composition since it is not necessary to isolate the respective amino acid derivatives produced by the above production process and since it may be superior in chelating activity and biodegradability to the amino acid derivatives isolated.

The chelating activity and biodegradability of the amino acid derivative composition of the present invention can be adjusted by adjusting the occurrence ratio between the above carboxylic acid adduct 1 and carboxylic acid adduct 2. Accordingly, when the amino acid derivative composition of the present invention is to be contained in a chelating agent, the chelating activity and biodegradability thereof can be adjusted according to the field of use thereof as a chelating agent and/or the performance characteristics required.

The occurrence ratio between the above carboxylic acid adduct 1 and carboxylic acid adduct 2 in the amino acid derivative composition of the present invention is generally 1:99 to 99:1. When the above occurrence ratio is outside the range of 1:99 to 99:1, it becomes impossible to adjust the chelating activity and biodegradability.

The above occurrence ratio is preferably 1:9 to 9:1.

When the above occurrence ratio is smaller than 1:9 and the proportion of the carboxylic acid adduct 1 becomes excessively small, the biodegradability decreases, hence it may become impossible to balance the biodegradability against the chelating activity. When the above occurrence ratio is greater than 9:1 and the proportion of the carboxylic acid adduct 1 becomes excessively large, the required chelating activity decreases, hence it may become impossible to balance the chelating activity against the biodegradability.

The above occurrence ratio is more preferably 2:8 to 8:2, still more preferably 3:7 to 7:3, most preferably 4:6 to 6:4.

The L-aspartic acid derivative represented by the above general formula (2) also has a sufficient level of chelating capacity and has particularly excellent biodegradability. Such an L-aspartic acid derivative constitutes another aspect of the present invention.

The term "L-aspartic acid derivative" as use herein does not mean a compound obtained by using L-aspartic acid as the starting material but only means that it is a compound having the basic skeleton of L-aspartic acid within the molecule.

One of the characteristic features from the chemical structure viewpoint of the L-aspartic acid derivative of the present invention is that at least four carboxyl or substituted carboxyl groups, a nitrogen atom and an ether group-derived oxygen atom or atoms occur simultaneously in one and the same molecule.

Owing to that feature from the chemical structure viewpoint, the L-aspartic acid derivative of the invention can serve as an at least hexadentate ligand against metal ions and therefore can exhibit good chelating activity. Among the L-aspartic acid derivatives covered by the present invention, those in which n is 0 and m is 2 can have a still increased coordination number against metal ions and therefore can exhibit still better chelating activity.

Among the L-aspartic acid derivatives according to the present invention, the compound in which n is 1, m is 1 and M is hydrogen and in which the asymmetric carbon atom carrying the symbol * has an unspecified configuration is the compound described as BCEEAA in Laid-open International Patent Specification WO 97/45395. However, while said BCEEAA has a total of three asymmetric carbon atoms in its molecule, the configuration of any of the three symmetric carbon atoms has not been specified, hence said BCEEAA should be construed as being a compound different from the L-aspartic acid derivative of the present invention in which the configuration for one asymmetric carbon atom has been specified. Further, since it is one of the structural features of the L-aspartic acid derivative of the present invention that one asymmetric carbon atom of which the configuration is specified is bonded to the tertiary amine-constituting nitrogen atom, the BCEEAA and the L-aspartic acid derivative of the present invention should be construed as being compounds different from each other. Furthermore, the L-aspartic acid derivative of the present invention differs in the effect as a chelating agent and, in particular, in biodegradability from BCEEAA and, therefore, the present invention is distinct from the invention described in the above-cited laid-open international patent specification.

The L-aspartic acid derivative of the present invention has excellent chelating activity as well as high biodegradability. As to why such excellent chelating activity and high biodegradability are exhibited, the same reasons as mentioned hereinabove may possibly be mentioned. Thus, it may be pointed out that the L-aspartic acid derivative of the invention has a plurality of groups having a chelating activity-enhancing effect. Further, the L-aspartic acid derivative of the invention has an asymmetric carbon atom showing an S configuration and, in its tertiary amine structure, the above asymmetric carbon atom in S configuration is bonded to the nitrogen atom and, when, for example, m in general formula (2) is 2 and n is 0, the derivative has a hydroxy group and, owing to the presence of such asymmetric carbon atom and hydroxy group, which are readily undergo biodegradation, it is probably biodegraded effectively. It is also conceivable that once asymmetric carbon and hydroxy group have been biodegraded, the biodegradation can proceed in a chain reaction manner, resulting in high biodegradability.

The L-aspartic acid derivative of the invention, which is represented by the general formula (2), when m is 1 and n is 1, for instance, becomes an L-aspartic acid derivative (A) represented by the general formula (3) and, when m is 2 and n is 0, it becomes an L-aspartic acid derivative (A) represented by the general formula (4). Therefore, the L-aspartic acid derivative of the invention includes two subclasses, namely the above L-aspartic acid derivative (A) and L-aspartic acid derivative (B).

One of the features of the L-aspartic acid derivative of the invention lies in that the asymmetric carbon atom carrying the mark * in the structural formula given as general formula (2) is in S configuration. While, in the general formula (2), there are three asymmetric carbon atoms, the configuration of the other asymmetric carbon atoms than the one marked with * need not be specific. The S configuration and R configuration may occur together without any restriction with regard to the occurrence ratio therebetween. Therefore, the L-aspartic acid derivative of the present invention is a compound in which the configuration of only the one asymmetric carbon atom marked with * out of the three asymmetric carbon atoms occurring in the molecule is specified as S.

When the L-aspartic acid derivative of the invention is produced by the process for producing L-aspartic acid derivatives according to the present invention, which is mentioned later herein, the configuration of the starting material L-aspartic acid is retained, hence the L-aspartic acid-derived configuration is retained as it is as the S configuration of the asymmetric carbon atom marked with * in the structural formula given as general formula (2).

The chelating activity and biodegradability of the L-aspartic acid derivative of the invention can be determined by various methods of measurement. For example, the measurement methods applicable to the amino acid derivative composition mentioned hereinabove can also be applied.

The process for producing the L-aspartic acid derivative of the invention is not particularly restricted but, for example, the derivative can be produced by following the above-mentioned process for producing amino acid derivatives and using L-aspartic acid as the amino acid, ethylene oxide as the alkylene oxide and maleic acid as the unsaturated carboxylic acid, namely by a process comprising the step of causing ethylene oxide to add to an L-aspartic acid derivative and the step of reacting the L-aspartic acid derivative-ethylene oxide adduct with maleic acid in the presence of a rare earth-based catalyst.

A typical example of each of the above steps is described below.

In the present specification, the step of causing ethylene oxide to add to an L-aspartic acid derivative is referred to also as "ethylene oxide addition step" and the step of reacting the L-aspartic acid derivative-ethylene oxide adduct with maleic acid in the presence of a rare earth-based catalyst is also referred to as "maleic acid addition step".

In the above reaction formula, X is as defined above.

As the above ethylene oxide adduct, there may generally be mentioned an ethylene oxide adduct (general formula (11) given above) resulting from complete substitution of the two hydrogen atoms of the amino group in L-aspartic acid by ethylene oxide. The thus-formed ethylene oxide adduct represented by the general formula (11) is generally subjected to maleic acid addition reaction to give the maleic acid adduct. As the thus-obtainable maleic acid adduct, there may be mentioned the maleic acid adduct 1 (general formula (12) given above) resulting from addition of one molecule of maleic acid and the maleic acid adduct 2 (general formula (13) given above) resulting from addition of two molecules of maleic acid.

The above L-aspartic acid derivative production process also constitutes an aspect of the present invention. According to the process of the invention, there is no possibility of formation of the compound represented by the above general formula (10) at all, as mentioned hereinabove. In this respect, the L-aspartic acid derivative production process of the present invention is quite different from the production process disclosed in Laid-open International Patent Specification WO 97/45396. The compound represented by the above general formula (10) is inferior in chelating activity and in biodegradability and a compound is quite different from the L-aspartic acid derivative of the present invention.

The reaction methods, inclusive of the starting material charge ratios and reaction conditions, in the above ethylene oxide addition step and maleic acid addition step are the same as those mentioned above referring to the alkylene oxide addition step and unsaturated carboxylic acid addition step. The composition obtained in the maleic acid addition step can be further separated into the respective components and each L-aspartic acid derivative can be isolated in the same manner as mentioned above.

The maleic acid adduct 1 represented by the general formula (12) as produced by the above L-aspartic acid derivative production process is the same compound as the L-aspartic acid derivative (A) of general formula (3) already mentioned hereinabove, while the maleic acid adduct 2 represented by the general formula (13) is the same compound as the L-aspartic acid derivative (B) of general formula (4) already mentioned hereinabove.

The L-aspartic acid derivative composition comprising the above L-aspartic acid derivative (A) and L-aspartic acid derivative (B) with an occurrence ratio therebetween lying in a specific range is a very useful composition since it is not necessary to isolate the respective L-aspartic acid derivatives and since the composition itself is equivalent or superior in chelating activity and biodegradability to the respective isolated L-aspartic acid derivatives. The above L-aspartic acid derivative composition also constitutes an aspect of the present invention.

The chelating activity and biodegradability of the above L-aspartic acid derivative composition can be adjusted by adjusting the occurrence ration between the above L-aspartic acid derivative (A) and L-aspartic acid derivative (B). Accordingly, when the above L-aspartic acid derivative composition is to be contained in a chelating agent, the chelating activity and biodegradability thereof can be adjusted according to the field of use thereof as a chelating agent and/or the performance characteristics required thereof.

The occurrence ratio between the L-aspartic acid derivative (A) and L-aspartic acid derivative (B) in the above L-aspartic acid derivative composition is generally 1:99 to 99:1. When the above occurrence ratio is outside the range of 1:99 to 99:1, it becomes impossible to adjust the chelating activity and biodegradability.

The above occurrence ratio is preferably 1:9 to 9:1.

When the above occurrence ratio is smaller than 1:9 and the proportion of the L-aspartic acid derivative (A) becomes excessively small, the biodegradability decreases, hence it may become impossible to balance the biodegradability against the chelating activity. When the above occurrence ratio is greater than 9:1 and the proportion of the L-aspartic acid derivative (A) becomes excessively large, the required chelating activity decreases, hence it may become impossible to balance the chelating activity against the biodegradability.

The above occurrence ratio is more preferably 2:8 to 8:2, still more preferably 3:7 to 7:3, most preferably 4:6 to 6:4.

As already mentioned, the L-aspartic acid derivative composition according to the present invention can be produced by a production process comprising the step of causing ethylene oxide to add to L-aspartic acid and the step of reacting the L-aspartic acid-ethylene oxide adduct with maleic acid in the presence of a rare earth-based catalyst. Such L-aspartic acid derivative production process is also an aspect of the present invention.

The amino acid derivative composition, L-aspartic acid derivative and L-aspartic acid derivative composition each has both chelating activity and biodegradability and therefore can be used in various chelating agents. The chelating agent comprising the amino acid derivative composition, L-aspartic acid derivative and/or L-aspartic acid derivative composition according to the present invention constitutes a further aspect of the present invention.

The chelating agent of the present invention may contain, in addition to the amino acid derivative composition, L-aspartic acid derivative and/or L-aspartic acid derivative composition of the present invention, another chelating agent and/or an additive or additives, etc.

The chelating agent of the present invention can be utilized in a wide range of fields, for example in detergents, detergent compositions, auxiliaries for textile industry, auxiliaries for paper and pulp manufacture, metal surface treating agents, photographic developers and the like.

The process for producing N-bishydroxyalkyl-amino acids represented by the above general formula (5) which comprises the step of causing an alkylene oxide to add to an amino acid salt in an aqueous solution can give the desired N-bishydroxyalkyl-amino acids in high yields while simplifying the production process and reducing the possibility of byproduct formation. Such N-bishydroxyalkyl-amino acid production process is also an aspect of the present invention.

The above step of causing an alkylene oxide to add to an amino acid salt in an aqueous solution is hereinafter referred to also as "alkylene oxide addition step (2)".

The amino acid salt mentioned above may be any amino acid salt having a chemical structure such that the hydrogen ion belonging to the carboxyl group in the-amino acid has been completely substituted by a cation such as a metal ion and an ammonium ion, without any particular restriction. When the amino acid has a plurality of carboxyl groups, for instance, it is preferred that the hydrogen ion at each of the plurality of carboxyl groups has totally been substituted by a sodium ion. Such amino acid salts may be used singly or two or more of them maybe used combinedly. Within limits within which the effects producible in accordance with the present invention are not sacrificed, the amino acid salt may contain a salt species having a chemical structure such that the hydrogen ions at the plurality of carboxyl groups in the amino acid has have been only partly substituted by a cation such as a metal ion and an ammonium ion.

The amino acid salt to be used in the practice of the present invention is not particularly restricted but includes, among others, salts of those amino acids mentioned hereinabove. The amino acids may be used singly or two or more of them may be used in combination. Among them, the use of an aspartic acid salt is preferred. The above amino acid salt may be optically active or inactive. Since, however, the L form is more inexpensive than the racemic form or D form, the L form is preferred. Further, since, as mentioned in detail later herein, the L form gives rise to N-bishydroxyalkyl-amino acids excellent in biodegradability, the L form is still more preferred. Therefore, in a most preferred mode of embodiment of the present invention, an L-aspartic acid salt is used.

The process for producing N-bishydroxyalkyl-amino acids according to the invention may comprise the step of preparing the above amino acid salt.

The step of preparing the above amino acid salt is not particularly restricted. For example, a procedure applicable in substituting the carboxyl hydrogen atom or atoms in the amino acid mentioned above can adequately be applied. In the step of preparing the above amino acid salt, it is preferred that the hydrogen ion at each carboxyl group of the amino acid be totally substituted.

In the above alkylene oxide addition step, the mole ratio between the amino acid salt and alkylene oxide is not particularly restricted but, for example, the ratio (number of moles of alkylene oxide)/(number of moles of amino acid salt) is preferably selected within the range of 2.0 to 4.5, more preferably 2.5 to 4.0, so that the yield of those N-bishydroxyalkyl-amino acids in which the two hydrogens of the amino group of the amino acid salt have totally been substituted by an alkylene oxide may be increased.

The reaction medium is not particularly restricted on the condition that it contains water. Thus, for example, water and mixed media composed of water and a water-soluble organic solvent such as an alcohol may be mentioned. Among them, water is preferably used.

The reaction conditions, the percent conversion of the amino acid salt and other parameters in the above alkylene oxide addition step (2) may be the same, for example, as those in the alkylene oxide addition step (1) mentioned hereinabove.

In the above alkylene oxide addition step (2), those N-bishydroxyalkyl-amino acids resulting from complete substitution of the two hydrogen atoms of the amino group in the amino acid salt by an alkylene oxide are generally formed. However, those N-bishydroxyalkyl-amino acids resulting from substitution of one hydrogen atom of the amino group in the amino acid salt by an alkylene oxide may also be formed.

The process for producing N-bishydroxyalkyl-amino acids according to the present invention may comprise, in addition to the above steps, the step of converting the cation at the carboxyl group or groups in the N-bishydroxyalkyl-amino acid produced in the above alkylene oxide addition step to another cation or the hydrogen ion.

The process for producing N-bishydroxyalkyl-amino acids according to the present invention comprises simplified production steps and therefor is advantageous from the production cost viewpoint. Further, the possibility of byproduct formation is low. Furthermore, since the reaction of the alkylene oxide is carried out in an aqueous solution, it is possible to submit to the reaction of an excessive number of moles of the alkylene oxide relative to the number of moles of the amino acid salt. Thus, the production steps are simplified, the possibility of byproduct formation is reduced and, as a result of synergism of these effects, the N-bishydroxyalkyl-amino acids can be produced efficiently in increased yields.

One of the structural features of the N-bishydroxyalkyl-amino acid produced in accordance with the present invention lies in that at least one carboxyl or substituted carboxyl group and a nitrogen atom simultaneously occur in one and the same molecule and therefore the acids can become at least bidendate against metal ions. As a result, they exhibit good chelating activity.

The above N-bishydroxyalkyl-amino acid has chelating activity and show high biodegradability. As to why such excellent chelating activity and high biodegradability can be exhibited, the same reasons as mentioned hereinabove may possibly be mentioned. Thus, it may be pointed out that the N-bishydroxyalkyl-amino acid of the present invention has a plurality of groups having a chelating activity-enhancing effect. Further, the N-bishydroxyalkyl-amino acid of the present invention has, in its tertiary amine structure, readily biodegradable hydroxy groups and therefore it is probably biodegraded effectively. It is also conceivable that once the hydroxy groups have been biodegraded, the biodegradation can proceed in a chain reaction manner, resulting in high biodegradability.

When the above N-bishydroxyalkyl-amino acid is produced through the step of causing an alkylene oxide to add to an L-form amino acid salt in an aqueous solution, the N-bishydroxyalkyl-amino acid of the present invention is represented, for example, by the general formula (14):

(14)

wherein R, $M^2$ and X are as defined above and * indicates that the asymmetric carbon atom bearing this mark is in S configuration.

In this case, the N-bishydroxyalkyl-amino acid has, in its chemical structure, an asymmetric carbon atom in S configuration and, in its tertiary amine structure, the asymmetric carbon atom in S configuration is bonded to the nitrogen atom and there are hydroxy groups and, as a result, said acid shows excellent biodegradability. Although the reasons therefor are not fully clear, it is presumable, for example, that since it has an asymmetric carbon atom in S configuration and, in its tertiary amine structure, has the asymmetric carbon atom in S configuration, which is readily biodegradable, bonded to the nitrogen atom and further has hydroxy groups, as mentioned above, it can be biodegraded effectively. It is further presumable that once such asymmetric carbon atom and hydroxy groups have been biodegraded, the biodegradation occurs in a chain reaction manner and, as a result, high biodegradability is exhibited.

The above process for producing N-bishydroxyalkyl-amino acids is useful, for example, as a process for producing compounds having the basic skeleton of an amino acid within the molecule, for example intermediates for the production of the amino acid derivative mentioned hereinabove, or as a preceding step in the process for producing the above-mentioned amino acid derivative. In this regard, the above process is a very useful one since the amino acid derivative composition and amino acid derivatives mentioned above can be produced by a process comprising the N-bishydroxyalkyl-amino acid derivative production process of the present invention in high yields while the production steps are simplified and the possibility of byproduct formation is reduced.

In this case, by using the above N-bishydroxyalkyl-amino acid represented of general formula (14) as an intermediate, it becomes possible, for the same reasons as mentioned above, to reduce the cost of production of the final product, namely the compound having the basic skeleton of an amino acid within the molecule, and it also becomes possible for said final product to have good biodegradability since the S configuration of the asymmetric carbon atom is maintained.

According to the above-mentioned process for producing N-bishydroxyethylaspartic acids of general formula (6) which comprises the step of causing ethylene oxide to add to an aspartic acid salt in an aqueous solution, the production steps are simplified, the possibility of byproduct formation is reduced, and N-bishydroxyethylaspartic acids can be produced in improved yields. Such N-bishydroxyethylaspartic acid production process is a further aspect of the present invention.

The above step of causing ethylene oxide to add to an aspartic acid salt in an aqueous solution is not particularly restricted but may be carried out according to the above-mentioned N-bishydroxyalkyl-amino acid production process using an aspartic acid salt as the amino acid salt and ethylene oxide as the alkylene oxide. The aspartic acid salt may be optically active or inactive. For the reasons mentioned hereinabove, however, the L form is preferred.

In the above step of causing ethylene oxide to add to an aspartic acid salt in an aqueous solution, the reaction procedure can be carried out in the same manner as in the above-mentioned N-bishydroxyalkyl-amino acid production process with respect to the reactant ratio, reaction conditions, amino acid salt conversion rate, byproduct, other steps, etc.

In the N-bishydroxyethylaspartic acid production process of the present invention as well, the same effects can be obtained as in the above-mentioned N-bishydroxyalkyl-amino acid production process.

One of the structural features of the N-bishydroxyethylaspartic acids produced in accordance with the present invention is that two carboxyl or substituted carboxyl groups and a nitrogen atom simultaneously occur in one and the same molecule, and can become a tri- or polydentate ligand against metal ions. Accordingly, they exhibit good chelating activity.

The above N-bishydroxyethylaspartic acids, too, have excellent chelating activity and high biodegradability.

When the above N-bishydroxyethylaspartic acids are produced by a process comprising the step of causing ethylene oxide to add to an aspartic acid salt, which is in L form, in an aqueous solution, the N-bishydroxyethylaspartic acids produced in accordance with the invention are represented by the general formula (15):

(15)

wherein X is as defined above and * indicates that the asymmetric carbon atom marked with this is in S configuration.

In this case, the N-bishydroxyethylaspartic acids have, in their chemical structure, an asymmetric carbon atom in S configuration and, in their tertiary amine structure, have the asymmetric carbon atom in S configuration bonded to a nitrogen atom and have hydroxy groups, so that they show excellent biodegradability. As the reasons therefor, the same reasons as those mentioned above in connection with the biodegradability of the N-bishydroxyalkyl-amino acid are presumable.

The above N-bishydroxyethylaspartic acid production process is further useful as a process for producing intermediates for the production of compounds having the basic skeleton of aspartic acid within the molecule, for example the above-mentioned amino acid derivative composition, or as a step preceding to the above-mentioned amino acid derivative production process.

In this case, when the above N-bishydroxyethylaspartic acids of general formula (15) are used as intermediates, the final products, namely compounds having the basic skeleton of aspartic acid within the molecule, are produced at a reduced cost, retain the S configuration of the asymmetric carbon atom, and have good biodegradability, for the same reasons as mentioned above.

The N-bishydroxyalkyl-amino acids according to the present invention and the compounds produced by using the same as intermediates are useful as chelating agents. Chelating agents comprising any of these compounds alone or, if necessary, together with another or other compounds having chelating activity and/or an additive or additives can be utilized in a wide range of fields, such as detergents, detergent compositions, textile auxiliaries, auxiliaries in paper and pulp manufacture, agents for metal surface treatment, photographic developers and the like.

The amino acid derivative composition of the present invention, which has the constitution mentioned above, has an excellent chelating effect as well as good biodegradability and is useful as a chelating agent free of the possibility of environmental pollution The N-bishydroxyalkyl-amino acid production process of the invention, which is constituted as mentioned above, simplifies the production steps, reduces the probability of byproduct formation and thus can give N-bishydroxyalkyl-amino acids in increased yields.

BSET MODE FOR CARRYING OUT THE INVENTION

The following examples illustrate the present invention in further detail. They are, however, by no means limitative of the scope of the invention.

PRODUCTION EXAMPLE 1

Ethylene Oxide Addition Step
Production of Disodium N,N-bishydroxyethylaspartate L-Aspartic acid (26.62 g, 0.2 mole) was added to 40 g of water and, after addition of 16.0 g of sodium hydroxide, water was added until a total weight of 88.56 g was obtained. This aqueous solution was charged in an autoclave and, after sufficient purging with nitrogen and heating to 40° C., 35.24 g (0.8 mole) of ethylene oxide was added over 3 hours. After completion of the addition, the system was further stirred for 1 hour at 40° C. and the ethylene oxide remaining in the system was removed, whereby 107.69 g of an aqueous solution was obtained. This reaction solution was analyzed by high-performance liquid chromatography, and the conversion of the starting material L-aspartic acid was found to be 100% and the content of disodium N,N-bishydroxyethylaspartate to be 53.02

PRODUCTION EXAMPLE 2

Maleic Acid Addition Step
Production of an L-aspartic Acid Derivative Composition Maleic anhydride (29.42 g, 0.3 mole), 24.0 g of sodium hydroxide and 4.89 g of lanthanum oxide were added to 53.85 g of the aqueous solution obtained in Production Example 1 and, after pH adjustment to 10.5, the mixture was concentrated to a total weight of 114.65 g. This solution was stirred at 90° C. for 8 hours, then 6.36 g of sodium carbonate was added, and the mixture was further stirred at 80° C. for 1 hour and then allowed to cool to room temperature. The resulting solid precipitate was filtered off and 114.82 g of an aqueous solution was obtained. Analysis of this aqueous solution revealed that the content of the desired L-aspartic acid derivative (A) was 28.89% by weight and that of the L-aspartic acid derivative (B) was 48.93% by weight.

PRODUCTION EXAMPLE 3

A 50-g portion of the reaction solution obtained in Production Example 2 was treated with DIAION PK216 (trademark; product of Mitsubishi Chemical), a strongly acidic cation exchange resin, and then subjected to a separation procedure using a column packed with DIAION PA316 (trademark; formic acid anion type; product of Mitsubishi Chemical), a strongly basic anion exchange resin, and aqueous solutions of formic acid (0 M to 2.5 M) as eluents, to give 6.86 g of the L-aspartic acid derivative (A) and 12.34 g of the L-aspartic acid derivative (B), each in the acid form.

EXAMPLES 1 AND 2 AND COMPARATIVE EXAMPLE 1

$Ca^{2+}$ chelating ability evaluation

Using the L-aspartic acid derivative (A) [Example 1] and L-aspartic acid derivative (B) [Example 2] obtained in Production Example 3 and [S,S]-ethylenediamine-N,N'-disuccinic acid (ss-EDDS) [Comparative Example 1] as the samples, $Ca^{2+}$ chelating ability evaluation was performed as mentioned above. The results are shown in Table 1. All the samples were used in the Na salt form and the ability was expressed in terms of weight of $CaCO_3$ trapped per gram of sample (mg $CaCO_3$/g)

TABLE 1

|  |  | $CaCO_3$ trapped per g sample (Na salt) |
|---|---|---|
| Ex. 1 | L-Aspartic acid deriv. (A) | 200 mg $CaCO_3$/g |
| Ex. 2 | L-Aspartic acid deriv. (B) | 280 mg $CaCO_3$/g |
| Compar. Ex. 1 | ss-EDDS (4 Na) | 160 mg $CaCO_3$/g |

In Table 1, ss-EDDS (4Na) denotes the Na salt form of ss-EDDS.

EXAMPLE 3 AND COMPARATIVE EXAMPLES 2 to 5

$H_2O_2$ Stabilization Test

Figure 1:
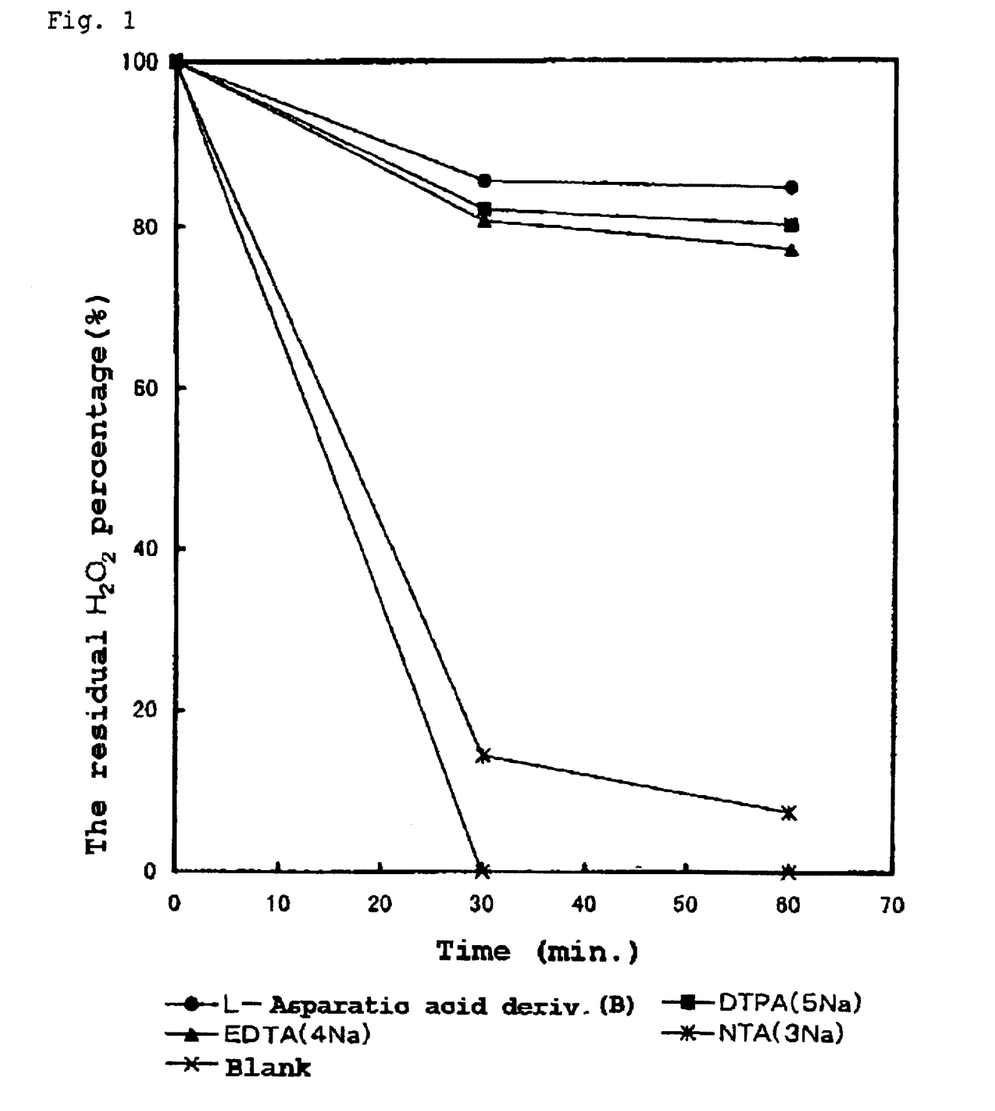
FIG. 1 is a graphic representation of the course of change with time of the residual $H_2O_2$ percentage (%) in an $H_2O_2$ stabilization test.

Using the L-aspartic acid derivative (B) [Example 3] obtained in Production Example 3, diethylenetriaminepentaacetic acid (DTPA) [Comparative Example 2], ethylenediaminetetraacetic acid (EDTA), [Comparative Example 3], nitrilotriacetic acid (NTA) [Comparative Example 4] and a blank (no chelating agent) [Comparative Example 5] as the samples, the $H_2O_2$ stabilization test mentioned above was carried out. The results are shown in Table 2 and FIG. 1. All the samples were used in the Na salt form.

TABLE 2

| Time (min.) | Example 3 L-Aspartic acid deriv. (B) | Compar. Ex. 2 DTPA (5 Na) | Compar. Ex. 3 EDTA (4 Na) | Compar. Ex. 4 NTA (3 Na) | Compar. Ex. 5 Blank (no chelating agent) |
|---|---|---|---|---|---|
| 0 | 100 | 100 | 100 | 100 | 100 |
| 30 | 85.5 | 82.1 | 80.7 | 14.4 | 0 |
| 60 | 84.6 | 80.1 | 77.1 | 7.5 | 0 |

In Table 2, DTPA (5Na), EDTA (4Na) and NTA (3Na) denotes the Na salt of DTPA, of EDTA and of NTA, respectively.

EXAMPLES 4 AND 5

Biodegradability Testing

The L-aspartic acid derivative (B) [Example 4] obtained in Production Example 3 and the optically inactive counterpart [Example 5], which has the same structure as the above derivative (B), as the samples, a biodegradability test was carried out according to the above-mentioned test method 301C: Modified MITI test (I). The results are shown in Table 3.

TABLE 3

| | Percent decomposition after 28 days based on residual DOC (%) |
|---|---|
| Example 4 | 35 |
| Example 5 | 10 |

In Table 3, each numerical value indicates the percent decomposition after 28 days based on the residual DOC.

What is claimed is:

1. An amino acid derivative composition which consists essentially of the S configuration of the amino acid derivatives as defined below of two or more kinds of amino acid derivatives represented by the general formula (1):

(1)

wherein R's are the same or different and each represents a hydrogen atom or an alkyl group containing 1 to 18 carbon atoms; $L^1$ represents —C*HX—$M^2$—X; $L^2$ represents —$CH_2$—$M^3$—X or —CHX—$M^4$—X; $M^2$, $M^3$ and $M^4$ are the same or different and each represents a straight or branched alkylene group containing 1 to 6 carbon atoms; X represents COOM; M's are the same or different and each represents a hydrogen atom, an alkali metal atom, an alkaline earth metal atom or an ammonium group; m represents an integer of 1 or 2 and n represents an integer of 0 or 1 on the condition that m+n is equal to 2; and * indicates that the asymmetric carbon atom carrying this symbol is in S configuration, said amino acid derivative composition being superior in biodegradability and chelating activity to racemic form having an unspecified configuration on the asymmetric carbon atom carrying the symbol.

2. A chelating agent which comprises an amino acid derivative composition consisting essentially of the S configuration of the amino acid derivative composition according to claim 1.

3. A chelating agent which comprises an aspartic acid derivative consisting essentially of the S configuration of an L-aspartic acid derivative as defined below of the general formula (2):

(2)

wherein X represents COOM; M's are the same or different and each represents a hydrogen atom, an alkali metal atom, an alkaline earth metal atom or an ammonium group; m represents an integer of 1 or 2 and n represents an integer of 0 or 1 on the condition that m+n is equal to 2; and

* indicates that the asymmetric carbon atom carrying this symbol is in S configuration.

4. An L-aspartic acid derivative composition which consists essentially of the S configuration of an L-aspartic acid derivative (A) and an L-aspartic acid derivative (B) as defined below,
said derivative (A) being represented by the general formula (3):

(3)

wherein X represents COOM, M's are the same or different and each represents a hydrogen atom, an alkali metal atom, an alkaline earth metal atom or an ammonium group and * indicates that the asymmetric carbon atom carrying this symbol is in S configuration,
and said derivative (B) being represented by the general formula (4):

(4)

wherein X represents COOM, M's are the same or different and each represents a hydrogen atom, an alkali metal atom, an alkaline earth metal atom or an ammonium group and * indicates that the asymmetric carbon carrying this symbol is in S configuration, wherein, in said L-aspartic acid derivative composition, the occurrence ratio (mole ratio) between said L-aspartic acid derivative (A) and said L-aspartic acid derivative (B) is in the range of 1:99 to 99:1, said L-aspartic acid derivative composition being superior in biodegradability and chelating activity to racemic form having an unspecified configuration on the asymmetric carbon atom carrying the symbol *.

5. A chelating agent which comprises an L-aspartic acid derivative composition consisting essentially of the S configuration of the L-aspartic acid derivative composition according to claim 4.

* * * * *

UNITED STATES PATENT AND TRADEMARK OFFICE
CERTIFICATE OF CORRECTION

PATENT NO.    : 6,504,054 B1
DATED         : January 7, 2003
INVENTOR(S)   : Sumida et al.

It is certified that error appears in the above-identified patent and that said Letters Patent is hereby corrected as shown below:

<u>Column 23,</u>
Line 42, "the symbol" change to -- the symbol* --

Signed and Sealed this

Thirteenth Day of May, 2003

JAMES E. ROGAN
*Director of the United States Patent and Trademark Office*